US010357656B2

(12) United States Patent
Heasman

(10) Patent No.: US 10,357,656 B2
(45) Date of Patent: Jul. 23, 2019

(54) HEARING PROSTHESIS PROGRAMMING

(71) Applicant: Cochlear Limited, Macquarie University, NSW (AU)

(72) Inventor: John Michael Heasman, Hampton (AU)

(73) Assignee: COCHLEAR LIMITED, Macquarie University (AU)

( * ) Notice: Subject to any disclaimer, the term of this patent is extended or adjusted under 35 U.S.C. 154(b) by 560 days.

(21) Appl. No.: 15/207,843

(22) Filed: Jul. 12, 2016

(65) Prior Publication Data

US 2018/0015287 A1    Jan. 18, 2018

(51) Int. Cl.
| | |
|---|---|
| *A61N 1/36* | (2006.01) |
| *A61B 5/04* | (2006.01) |
| *A61B 5/12* | (2006.01) |
| *A61N 1/05* | (2006.01) |
| *H04R 25/00* | (2006.01) |
| *A61B 5/00* | (2006.01) |

(52) U.S. Cl.
CPC .......... *A61N 1/36036* (2017.08); *A61B 5/04* (2013.01); *A61B 5/04001* (2013.01); *A61B 5/12* (2013.01); *A61B 5/125* (2013.01); *A61B 5/6817* (2013.01); *A61N 1/0541* (2013.01); *A61N 1/36038* (2017.08); *A61N 1/36039* (2017.08); *H04R 25/606* (2013.01); *H04R 25/70* (2013.01)

(58) Field of Classification Search
CPC ............ A61N 1/0541; A61N 1/36036; A61N 1/36038; A61N 1/36039; A61B 5/04; A61B 5/04001; A61B 5/12; A61B 5/121; A61B 5/125; A61B 5/126
See application file for complete search history.

(56) References Cited

U.S. PATENT DOCUMENTS

| | | | |
|---|---|---|---|
| 6,157,861 | A | 12/2000 | Faltys |
| 6,208,882 | B1 | 3/2001 | Lenarz et al. |

(Continued)

FOREIGN PATENT DOCUMENTS

| | | |
|---|---|---|
| CA | 2556292 A1 | 4/2006 |
| CN | 103636234 A | 3/2014 |

(Continued)

OTHER PUBLICATIONS

T. Van Den Abbeele et al., "Multicentre investigation on electrically evoked compound action potential and stapedius Reflex: how do these objective measures relate to implant programming parameters?", Cochlear Implants International: An Interdisciplinary Journal, vol. 13, Issue 1, 2012, DOI: 10.1179/1754762810Y.0000000001, 10 pages.

(Continued)

*Primary Examiner* — Eugene T Wu
(74) *Attorney, Agent, or Firm* — Edell, Shapiro & Finnan, LLC

(57) ABSTRACT

Presented herein are objective techniques for determining the upper limit of the dynamic range (i.e., the comfort level) of implanted stimulating contacts through the use of electrocochleography (ECoG) measurements to indirectly detect the onset and duration of a recipient's stapedius reflex. In particular, stimulation is delivered to a recipient's cochlea to trigger the onset of the stapedius reflex and the resulting acoustic impedance change is detected by monitoring the acoustically evoked ECoG.

20 Claims, 8 Drawing Sheets

(56) References Cited

U.S. PATENT DOCUMENTS

| | | | |
|---|---|---|---|
| 6,415,185 B1* | 7/2002 | Maltan | A61N 1/36036 |
| | | | 607/57 |
| 6,496,734 B1 | 12/2002 | Money | |
| 7,206,640 B1 | 4/2007 | Overstreet | |
| 8,160,715 B2 | 4/2012 | Schmidt et al. | |
| 8,165,687 B2 | 4/2012 | Cornejo Cruz et al. | |
| 8,694,113 B2 | 4/2014 | Smoorenburg | |
| 8,768,477 B2 | 7/2014 | Spitzer et al. | |
| 8,892,212 B2 | 11/2014 | Kals et al. | |
| 8,954,159 B2 | 2/2015 | Nopp et al. | |
| 9,084,894 B2 | 7/2015 | Kals | |
| 2008/0086184 A1 | 4/2008 | Schmidt et al. | |
| 2008/0195179 A1* | 8/2008 | Quick | A61B 5/121 |
| | | | 607/57 |
| 2009/0018616 A1* | 1/2009 | Quick | A61B 5/121 |
| | | | 607/57 |
| 2012/0109006 A1 | 5/2012 | James | |
| 2013/0006042 A1 | 1/2013 | Hillbratt et al. | |
| 2014/0100471 A1 | 4/2014 | Hessler et al. | |
| 2014/0107441 A1* | 4/2014 | Grasso | A61B 5/125 |
| 2015/0005843 A1 | 1/2015 | Polak | |
| 2015/0051654 A1 | 2/2015 | Litvak et al. | |
| 2015/0057714 A1 | 2/2015 | Litvak et al. | |
| 2018/0229035 A1* | 8/2018 | Koka | A61N 1/36039 |
| 2019/0046116 A1* | 2/2019 | Shah | A61B 5/1104 |

FOREIGN PATENT DOCUMENTS

| | | | |
|---|---|---|---|
| EP | 1737533 A2 | 1/2007 | |
| EP | 2480128 A2 | 8/2012 | |
| WO | 2008/033791 A1 | 3/2008 | |
| WO | 2012/129465 A1 | 9/2012 | |
| WO | 2012/158486 A2 | 11/2012 | |
| WO | 2012/162349 A1 | 11/2012 | |
| WO | 2013/043952 A1 | 3/2013 | |
| WO | 2013/081997 A1 | 6/2013 | |
| WO | 2014/055823 A1 | 4/2014 | |
| WO | 2014/210415 A1 | 12/2014 | |
| WO | WO-2017100866 A1 * | 6/2017 | A61B 5/04 |

OTHER PUBLICATIONS

J.H.J. Allum et al., "Relationship of intraoperative electrically evoked stapedius reflex thresholds to maximum comfortable loudness levels of children with cochlear implants: Relaciones entre los umbrales transguirürgicos del reflejo estapedial eléctricamente evocado y los niveles máximos de sonoridad agradable en niños con implantes cocleares", International Journal of Audiology, vol. 41, Issue 2, 2002, DOI: 10.3109/14992020209090399, 8 pages.

W. H. Shapiro et al., "Remote Intraoperative Monitoring During Cochlear Implant Surgery Is Feasible and Efficient", Otology & Neurotology, vol. 29, Issue 4, Jun. 2008, pp. 495-498, 4 pages.

E. Karatas et al., "Intraoperative electrically evoked stapedius reflex thresholds in children undergone cochlear implantation: Round window and cochleostomy approaches", International Journal of Pediatric Otorhinolaryngology, vol. 75, Issue 9, pp. 1123-1126, Sep. 2011, 4 pages.

B. Almqvist et al., "Objective Intraoperative Method to RecordAveraged Electromyographic Stapedius Muscle Reflexes in Cochlear Implant Patients", Audiology, vol. 39 No. 3, Original Article, Mar. 23, 2000, 7 pages.

T. J. Balkany et al., "Cochlear Implants in Children—A Review", Review Article, Ada Otolaryngol 2002; 122: 356-362, Taylor & Francis healthsciences, ISSN 0001-6489, downloaded from informahealthcare.com on Jan. 28, 2013, 7 pages.

John A. Ferraro, "Electrocochleography: A Review of Recording Approaches, Clinical Applications, and New Findings in Adults and Children", DOI: 10.3766/jaaa.12.3., J Am Acad Audiol 21:145-152 (2010), Journal of the American Academy of Audiology, vol. 21, No. 3, 2010, 8 pages.

G. Caner et al., "Optimizing Fitting in Children Using Objective Measures Such as Neural Response Imaging and Electrically Evoked Stapedius Reflex Threshold", Otology & Neurotology, vol. 28, No. 5, 2007, 28:637-640 © 2007, Otology & Neurotology, Inc., 4 pages.

K. Stephan et al., "Post-operative Stapedius Reflex Tests with Simultaneous Loudness Scaling in Patients Supplied with Cochlear Implants", Original Article, Audiology 2000; 39:13-18, Audiology, vol. 39 No. 1, DOI: 10.3109/002060900009073049, 6 pages.

B. van den Borne et al., "Stapedius Reflex Measurements During Surgery for Cochlear Implantation in Children", The American Journal of Otology, 17:554-558 © 1996, The American Journal of Otology, vol. 17, No. 4, 1996, 5 pages.

Aimee Gross, "Filling Techniques for the Pediatric Cochlear Implant Patient", AudiologyOnline, May 12, 2003, http://www.audiologyonline.com/articles/fitting-techniques-for-pediatric- . . . , 10 pages.

L. Buckler et al., "Relationship between Electrical Stapedial Reflex Thresholds and HiRes™ Program Settings: Potential Tool for Pediatric Cochlear-Implant Fitting", Jun. 2003, Valencia (CA): Advanced Bionics, 3 pages.

Michelle Hughes, "Objective Measures in Cochlear Implants", Plural Publishing, Jul. 13, 2012, https://books.google.com/books?id=xpU1BwAAQBAJ, Google Books, Preview, 1 page.

H. Cooper et al., "Cochlear Implants: A Practical Guide", John Wiley & Sons, May 1, 2006, Google Books, Preview, https://books.google.com/books?id=j9FhJoFPW-0C, 1 page.

J. Wolfe et al., "Programming Cochlear Implants", Plural Publishing, Oct. 31, 2014, Google Books, Preview, https://books.google.com/books?id=89wzBwAAQBAJ, 1 page.

J. Kosaner et al., "The Use of ESRT in Fitting Children with Cochlear Implants", Original Article, Int. Adv. Otol. 2009; 5:(1) 70-79, 10 pages.

A. Walkowiak et al., "ESRT, ART and MCL correlations in experienced paediatric cochler implant users", Cochlear Implants International: An Interdisciplinary Journal, vol. 11, Supplement 1, 2010, DOI: 10.1179/146701010X12671177204741, 4 pages.

International Search Report and Written Opinion in corresponding International Application No. PCT/IB2017/053838, dated Nov. 14, 2017, 12 pages.

* cited by examiner

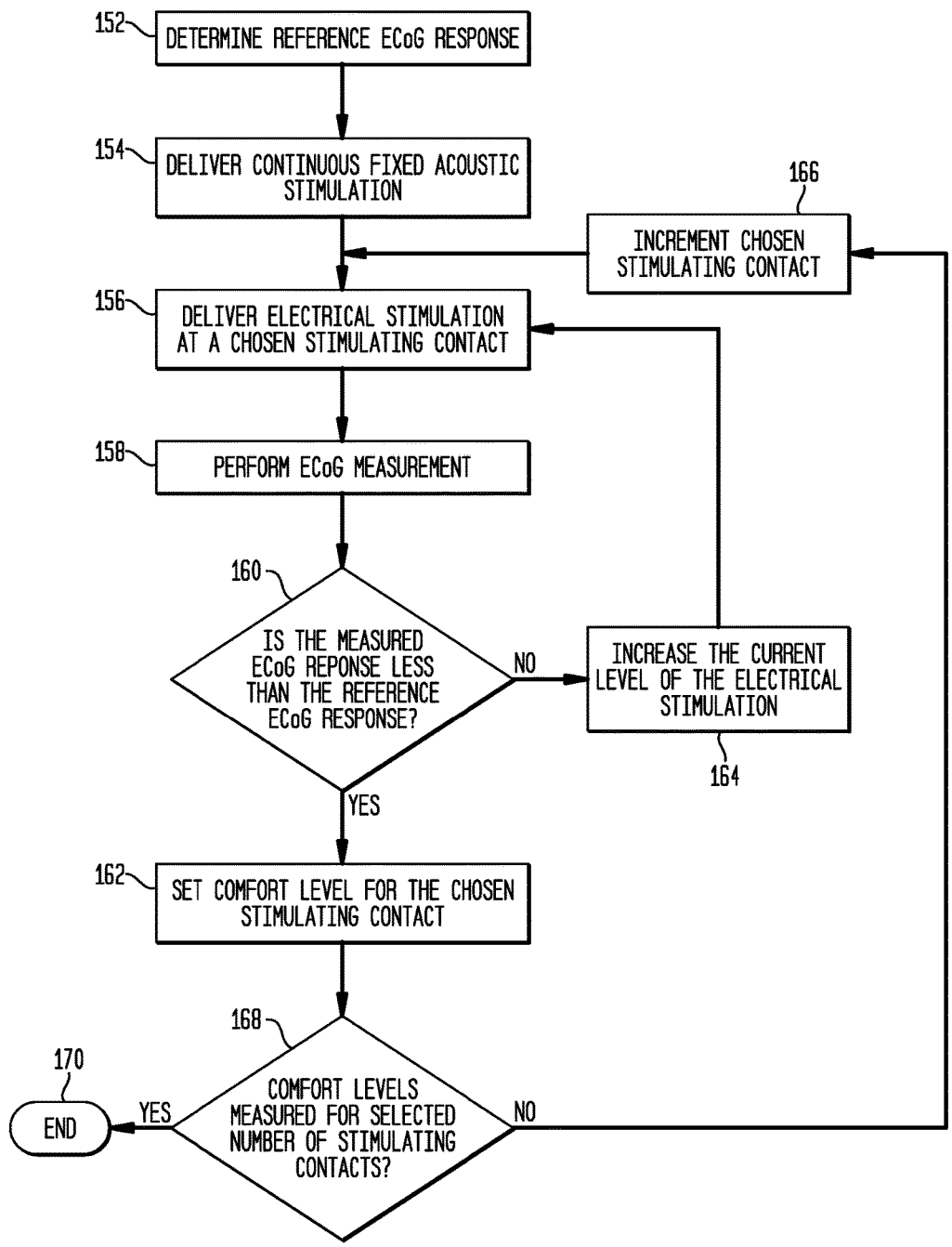

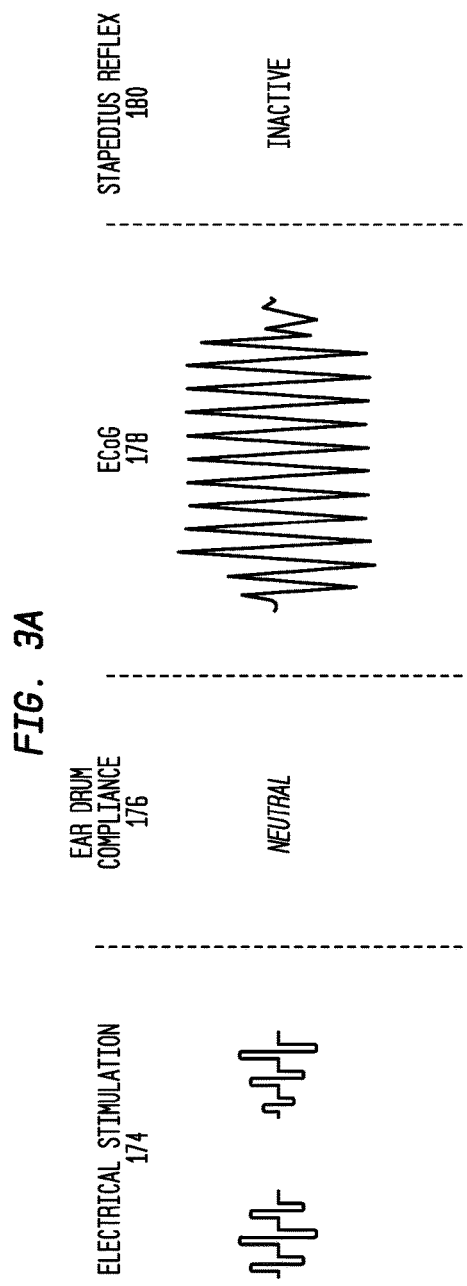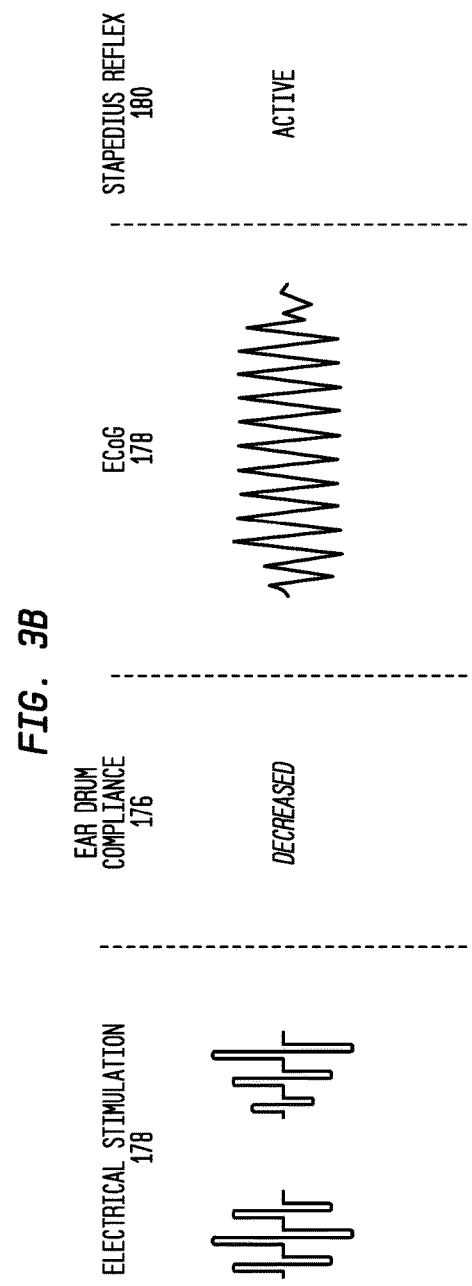

HEARING PROSTHESIS PROGRAMMING

BACKGROUND

Field of the Invention

The present invention relates generally to hearing prostheses.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates pressure waves within the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of stimulating auditory prosthesis that might also be proposed when a recipient experiences sensorineural hearing loss due to damage to the auditory nerve.

Certain individuals suffer from only partial sensorineural hearing loss and, as such, retain at least some residual hearing. These individuals may be candidates for electro-acoustic hearing prostheses.

SUMMARY

In one aspect, a method is provided. The method comprises: delivering acoustic test stimulation to a recipient of a hearing prosthesis; while the acoustic test stimulation is delivered to the recipient, sequentially delivering sets of electrical test stimulation, at incrementally increasing current levels, to a cochlea of a recipient via a selected intra-cochlear stimulating contact; performing one or more electrocochleography (ECoG) measurements in response to the delivery of each set of electrical test stimulation; and determining, based on at least one of the one or more ECoG measurements, a behavioural comfort level for the recipient at the selected intra-cochlear stimulating contact.

In another aspect, a method is provided. The method comprises: simultaneously delivering acoustic stimulation and electrical stimulation to a cochlea of a recipient, wherein the electrical stimulation is delivered via a first intra-cochlear stimulating contact; incrementally increasing a current level of the electrical stimulation delivered via the first intra-cochlear stimulating contact; and monitoring an acoustic impedance of the cochlea in response to the incrementally increasing current levels via electrocochleography (ECoG) measurements.

In another aspect, a hearing prosthesis system is provided. The hearing prosthesis system comprises: a receiver configured to deliver an acoustic signal to a cochlea of a recipient; a plurality of stimulating contacts configured to be positioned in the cochlea of the recipient, wherein a first one of the plurality of stimulating contacts is configured to sequentially deliver groups of current pulses to the cochlea at incrementally increasing current levels; one or more amplifiers configured to obtain, via at least a second one of the plurality of stimulating contacts, acoustically-evoked electrical potentials from the cochlea following delivery of each group of current pulses; and one or more processors configured to determine, based on the acoustically-evoked electrical potentials, an upper limit of a dynamic range associated with the first stimulating contact.

BRIEF DESCRIPTION OF THE DRAWINGS

Embodiments of the present invention are described herein in conjunction with the accompanying drawings, in which:

FIG. 2 is a detailed flowchart of a method in accordance with embodiments presented herein.

FIGS. 3A and 3B are schematic diagrams illustrating an indirect relationship between electrocochleography (ECoG) responses and a recipient's stapedius reflex;

DETAILED DESCRIPTION

Figure 1A:
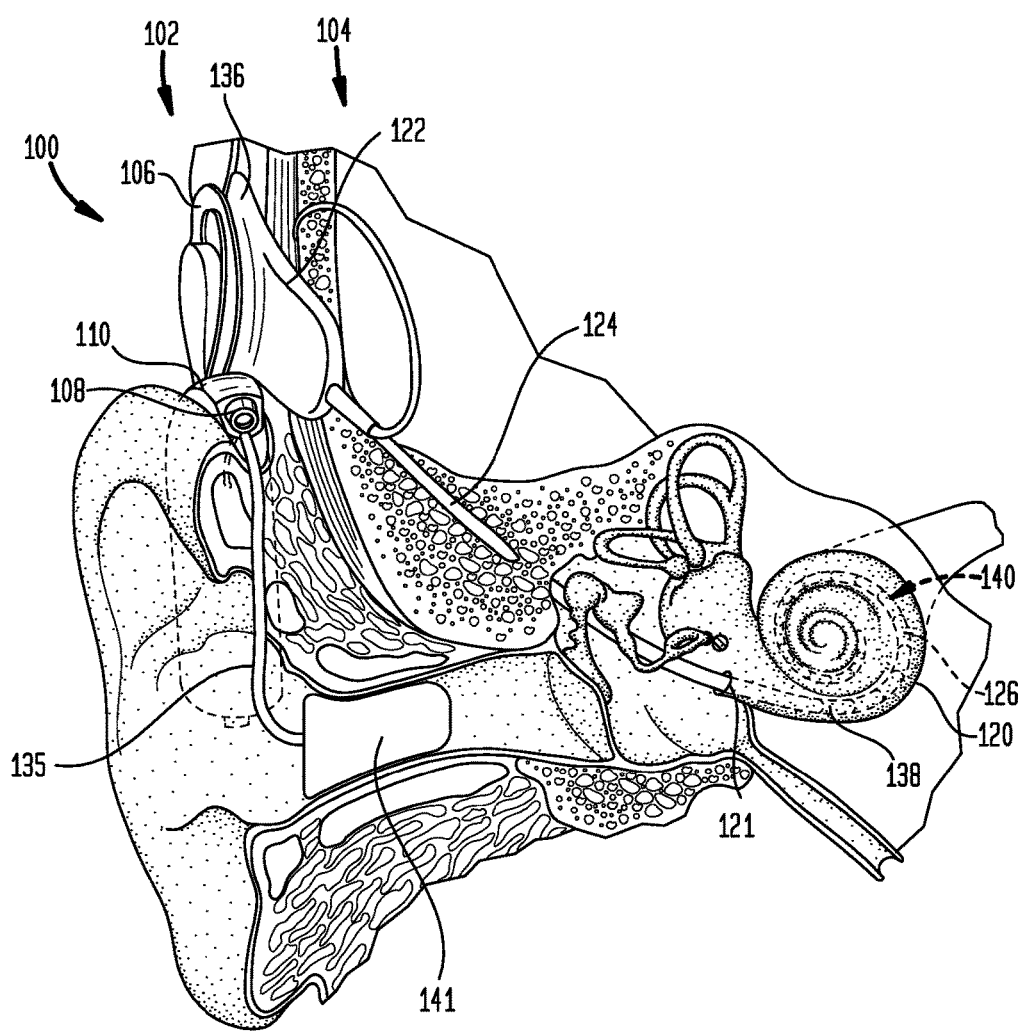
FIG. 1A is a schematic diagram of an electro-acoustic hearing prosthesis in accordance with embodiments presented herein.

Electrically-stimulating hearing prostheses, such as cochlear implants, electro-acoustic hearing prosthesis, auditory brainstem implants, etc., operate by converting at least a portion of received sound signals into electrical stimulation signals (current signals) for delivery to a recipient's auditory system. The window/range of electrical amplitudes (current levels) at which electrical stimulation signals may be delivered to the recipient's auditory system is limited. In particular, if the amplitude of the electrical stimulation signals is too low, then the associated sounds used to generate the electrical stimulation signals will not be perceived by the recipient (i.e., the stimulation signals will either not evoke a neural response in the cochlea or evoke a neural response that cannot be perceived by the recipient). Conversely, if the amplitude of the electrical stimulation signals is too high, then the associated sounds used to generate the electrical stimulation signals will be perceived as too loud or uncomfortable by the recipient. As such, electrical stimulation signals are generally delivered between a lower limit, referred to as a "threshold level," at which the associated sound signals are barely audible to the recipient, and an upper limit, referred to as a "comfort level," above which the associated sound signals are uncomfortably loud to the recipient. The difference in electrical amplitudes between the threshold level and the comfort level is referred to herein as the "dynamic range."

Due to, for example, anatomical features, insertion depth, etc., the dynamic range may be different for different stimulating contacts implanted in a recipient. That is, different stimulating contacts implanted in a recipient may have different associated threshold and comfort levels.

The range in acoustic amplitudes of sound signals received by an electrically-stimulating hearing prosthesis is considerably larger than the dynamic range associated with a stimulating contact. As such, the conversion of the received sound signals into electrical stimulation signals for delivery to the recipient includes, among other operations, mapping (compression) of the acoustic amplitudes into electrical amplitudes within the dynamic range of the corresponding stimulating contact(s) (i.e., the stimulating contact(s) at which the electrical stimulation is delivered to the recipient).

Since the threshold and comfort levels are dependent upon recipient-specific characteristics/behavior, and may be different across different stimulating contacts (electrodes), the stimulating contact dynamic ranges are determined for each recipient. In conventional/standard techniques, the threshold and comfort levels are determined within a clinical environment, typically using complex equipment and techniques implemented by trained audiologists/clinicians. These conventional clinical fitting/programming procedures may be difficult to administer to young children and other recipients that are unable to communicate effectively. Presented herein are objective techniques for determining the upper limit of the dynamic range (i.e., the comfort level) of implanted stimulating contacts through the use of electrocochleography (ECoG) measurements to indirectly detect the onset and duration of a recipient's stapedius reflex, also known as the acoustic reflex. In one embodiment, electrical stimulation is delivered at incrementally increasing current levels to a recipient's cochlea in order to trigger the onset of the stapedius reflex. The acoustic impedance resulting from the stapedius reflex change is detected by monitoring the acoustically evoked ECoG. In another embodiment, acoustic stimulation is delivered at incrementally increasing amplitudes to a recipient's cochlea in order to trigger the onset of the stapedius reflex and, again, the resulting acoustic impedance change is detected by monitoring the acoustically evoked ECoG. These fully integrated in-situ stapedius reflex measurements provide a convenient and effective objective mechanism for determination of a recipient's comfort levels at different stimulating contacts. The techniques presented herein can be either run by an operator or may be run fully automated in the clinical or the remote environment, possibly without supervision and hence may be applicable for both children and adults.

For ease of illustration, embodiments are primarily described herein with reference to one specific type of electrically-stimulating hearing prosthesis, namely an electro-acoustic hearing prosthesis comprising a cochlear implant portion and a hearing aid portion. However, it is to be appreciated that the techniques presented herein may be used with other types of electrically-stimulating hearing prostheses, such as cochlear implants, auditory brainstem implants, bi-modal hearing prostheses, and/or electro-acoustic hearing prosthesis comprising other types of output devices (e.g., auditory brainstem stimulators portions, direct acoustic stimulator portions, bone conduction device portions, etc.).

Figure 1B:
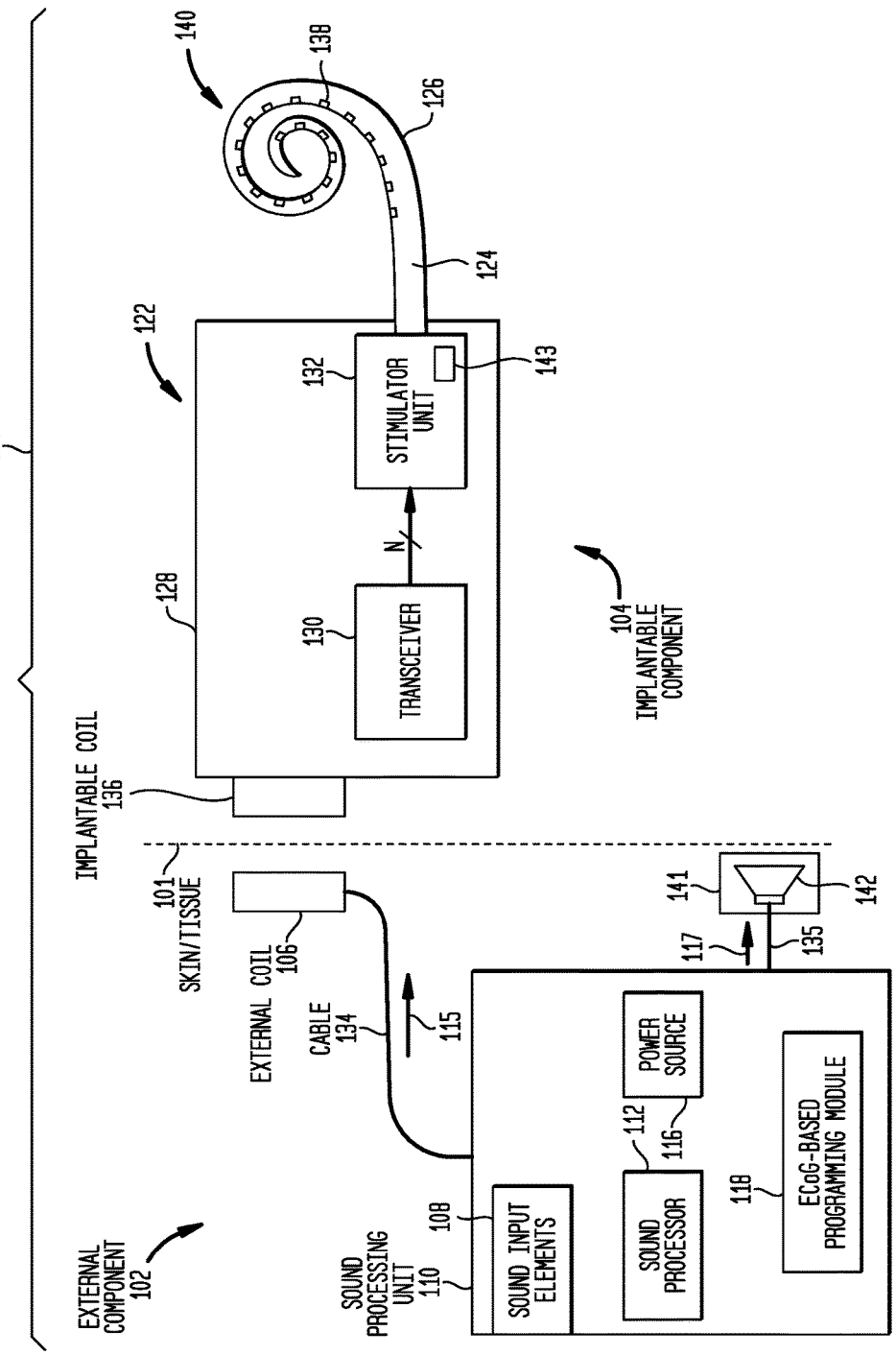
FIG. 1B is a block diagram of the electro-acoustic hearing prosthesis of FIG. 1A.

FIGS. 1A and 1B are diagrams of an illustrative implantable electro-acoustic hearing prosthesis configured to implement the techniques presented herein. More specifically, FIGS. 1A and 1B illustrate an electro-acoustic hearing prosthesis 100 that includes an external component 102 and an internal/implantable component 104. The external component 102 is configured to be directly or indirectly attached to the body of a recipient, while the implantable component 104 is configured to be subcutaneously implanted within the recipient (i.e., under the skin/tissue 101 of the recipient).

The external component 102 comprises a sound processing unit 110, an external coil 106, and, generally, a magnet (not shown in FIG. 1A) fixed relative to the external coil 106. The external coil 106 is connected to the sound processing unit 110 via a cable 134. The sound processing unit 110 comprises one or more sound input elements 108 (e.g., microphones, audio input ports, cable ports, telecoils, a wireless transceiver, etc.,) a sound processor 112, a power source 116, and an electrocochleography (ECoG)-based programming module 118. The sound processing unit 110 may be, for example, a behind-the-ear (BTE) sound processing unit, a body-worn sound processing unit, a button sound processing unit, etc.

Connected to the sound processing unit 110 via a cable 135 is a hearing aid component 141. The hearing aid component 141 includes a receiver 142 (FIG. 1B) that may be, for example, positioned in or near the recipient's outer ear. The receiver 142 is an acoustic transducer that is configured to deliver acoustic signals (acoustic stimulation signals) to the recipient via the recipient's ear canal and middle ear.

As shown in FIG. 1B, the implantable component 104 comprises an implant body (main module) 122, a lead region 124, and an elongate intra-cochlear stimulating assembly 126. The implant body 122 generally comprises a hermetically-sealed housing 128 in which an internal transceiver unit (transceiver) 130 and a stimulator unit 132 are disposed. The implant body 122 also includes an internal/implantable coil 136 that is generally external to the housing 128, but which is connected to the transceiver 130 via a hermetic feedthrough (not shown in FIG. 1B). Implantable coil 136 is typically a wire antenna coil comprised of multiple turns of electrically insulated single-strand or multi-strand platinum or gold wire. The electrical insulation of implantable coil 136 is provided by a flexible molding (e.g., silicone molding), which is not shown in FIG. 1B. Generally, a magnet is fixed relative to the implantable coil 136.

Elongate stimulating assembly 126 is configured to be at least partially implanted in the recipient's cochlea 120 (FIG. 1A) and includes a plurality of longitudinally spaced intra-cochlear electrical stimulating contacts (electrodes) 138 that collectively form a contact array 140 for delivery of electrical stimulation (current) to the recipient's cochlea.

Stimulating assembly 126 extends through an opening 121 in the cochlea (e.g., cochleostomy, the round window, etc.) and has a proximal end connected to stimulator unit 132 via lead region 124 and a hermetic feedthrough (not shown in FIG. 1B). Lead region 124 includes a plurality of conductors (wires) that electrically couple the electrodes 138 to the stimulator unit 132.

Returning to external component 102, the sound input element(s) 108 are configured to detect/receive input sound signals and to generate electrical input signals therefrom. The sound processor 112 is configured execute sound processing and coding to convert the electrical input signals received from the sound input elements into output signals that represent acoustic and/or electric (current) stimulation for delivery to the recipient. That is, as noted, the electro-acoustic hearing prosthesis 100 operates to evoke perception by the recipient of sound signals received by the sound input elements 108 through the delivery of one or both of electrical stimulation signals and acoustic stimulation signals to the recipient. As such, depending on a variety of factors, the sound processor 112 is configured to convert the electrical input signals received from the sound input elements into a first set of output signals representative of electrical stimulation and/or into a second set of output signals representative of acoustic stimulation. The output signals representative of electrical stimulation are represented in FIG. 1B by arrow 115, while the output signals representative of acoustic stimulation are represented in FIG. 1B by arrow 117.

The output signals 115 are, in the examples of FIGS. 1A and 1B, encoded data signals that are sent to the implantable component 104 via external coil 106. More specifically, the magnets fixed relative to the external coil 106 and the implantable coil 136 facilitate the operational alignment of the external coil 106 with the implantable coil 136. This operational alignment of the coils enables the external coil 106 to transmit the encoded data signals, as well as power signals received from power source 116, to the implantable coil 136. In certain examples, external coil 106 transmits the signals to implantable coil 136 via a radio frequency (RF) link. However, various other types of energy transfer, such as infrared (IR), electromagnetic, capacitive and inductive transfer, may be used to transfer the power and/or data from an external component to an electro-acoustic hearing prosthesis and, as such, FIG. 1B illustrates only one example arrangement.

In general, the encoded data and power signals are received at the transceiver 130 and are provided to the stimulator unit 132. The stimulator unit 132 is configured to utilize the encoded data signals to generate electrical stimulation signals (e.g., current signals) for delivery to the recipient's cochlea via one or more stimulating contacts 138. In this way, electro-acoustic hearing prosthesis 100 electrically stimulates the recipient's auditory nerve cells, bypassing absent or defective hair cells that normally transduce acoustic vibrations into neural activity, in a manner that causes the recipient to perceive one or more components of the received sound signals.

As noted above, it is common for hearing prosthesis recipients to retain at least part of this normal hearing functionality (i.e., retain at least one residual hearing). Therefore, the cochlea of a hearing prosthesis recipient can be acoustically stimulated upon delivery of a sound signal to the recipient's outer ear. In the example of FIGS. 1A and 1B, the receiver 142 is used to provide the acoustic stimulation. That is, the receiver 142 is configured to utilize the output signals 117 to generate acoustic stimulation signals that are provided to the recipient's cochlea via the middle ear bones and oval window, thereby creating waves of fluid motion of the perilymph within the cochlea.

Although FIGS. 1A and 1B illustrate the use of a receiver 142 to deliver acoustic stimulation to the recipient, it is to be appreciated that other types of devices may be used in other embodiments. It is also to be appreciated that embodiments of the present invention may be implemented in other hearing prostheses and other arrangements that that shown in FIGS. 1A and 1B.

With electrical stimulation, the volume of a sound signal perceived by the recipient depends on the level of the stimulus current delivered to the recipient upon receiving the sound signal (i.e., the amplitude of the electrical stimulation associated with the sound signal). In general, as the level of the delivered current increases, the loudness of the sound signal, as perceived by the recipient, increases. As such, the level of the stimulus current depends on a sound pressure level (SPL) of the sound signal as received by the sound inputs 108. The sound pressure levels of received sound signals may be received at different acoustic levels, which include an acoustic threshold level and an acoustic comfort level. The acoustic threshold level, referred to herein as the output or dynamic threshold SPL (TSPL), represents the SPL of sound signals below which amplification is needed to allow the recipient to perceive the sound signals. The acoustic comfort level, referred to herein as the output or dynamic comfort SPL (CSPL), represents the SPL of the sound above which the sound becomes uncomfortably loud. Between the dynamic TSPL and the dynamic CSPL, the log outputs increase approximately linearly with the log-SPL inputs.

As noted, the dynamic range for a stimulating contact 138 (i.e., the range of amplitudes at which electrical stimulation may be delivered) is a difference between a threshold level (T-Level) (i.e., a stimulus current that results in the recipient just being able to hear a sound at a given frequency) and a comfort level (C-Level) (i.e., a stimulus current applied by the stimulating contact to the recipient's cochlea that results in a sound with a certain pitch percept that the recipient can perceive comfortably). As such, when an electro-acoustic hearing prosthesis, such as electro-acoustic hearing prosthesis 100, converts received sound signals into electrical stimulation signals, the conversion includes, among other operations, mapping (compression) of the acoustic amplitudes (i.e., SPLs) into current levels within the recipient's dynamic range. More specifically, for a sound signal having an SPL that is less than the output TSPL, the sound signal will be mapped to below the T-Level, and not perceived. For a sound signal having an SPL that is between the dynamic TSPL and the dynamic CSPL, the stimulus current varies approximately linearly with the SPL (dB) of the sound. For a sound signal having an SPL greater than the dynamic CSPL (or C-Level), the stimulus current is typically fixed at the C-Level. In other words, the dynamic CSPL is the saturation level for the electrode. As such, accurate determination of the threshold and comfort levels for a recipient at the stimulating contacts (i.e., the anatomical location of the stimulating contact), referred to herein as "stimulating contact threshold levels" and "stimulating contact comfort levels," respectively, is important for proper delivery of electrical stimulation to a recipient. Determining stimulating contact threshold and comfort levels for a recipient is part of a fitting or programming process for the hearing prosthesis.

As noted, the electro-acoustic hearing prosthesis 100 also comprises the electrocochleography (ECoG)-based programming module 118. As described further below, the ECoG-based programming module 118 is configured to use acoustically evoked electrocochleography (ECoG) measurements to determine, in situ, stimulating contact comfort levels. As used herein, an ECoG measurement refers to the capture of a set of acoustically-invoked potentials, sometimes referred to herein as cochlear potentials or inner ear potentials, generated in a recipient's cochlea in response to the delivery of acoustic stimulation to the cochlea. A captured set of acoustically-invoked cochlear potentials i.e., an ECoG response) may include a plurality of different stimulus related potentials, such as the cochlear microphonic (CM), the cochlear summating potential (SP), the auditory nerve neurophonic (ANN), and the auditory nerve or Compound Action Potential (CAP), and higher order potentials (e.g., evoked potentials from the brainstem and the auditory cortex), which are measured independently or in various combinations.

The cochlear microphonic is an alternating current (AC) voltage that mirrors the waveform of the acoustic stimulus at low, moderate, and high levels of acoustic stimulation. The cochlear microphonic is generated by the outer hair cells of the organ of Corti and is dependent on the proximity of the recording electrode(s) to the stimulated hair cells and the basilar membrane. In general, the cochlear microphonic is proportional to the displacement of the basilar membrane by the travelling wave phenomena.

The summating potential is the direct current (DC) response of the outer hair cells of the organ of Corti as they move in conjunction with the basilar membrane (i.e., reflects the time-displacement pattern of the cochlear partition in response to the stimulus envelope). The summating potential is the stimulus-related potential of the cochlea and can be seen as a DC (unidirectional) shift in the cochlear microphonic baseline. The direction of this shift (i.e., positive or negative) is dependent on a complex interaction between stimulus parameters and the location of the recording electrode(s).

The auditory nerve neurophonic is a signal recorded from the auditory nerve, while the auditory nerve Action Potential represents the summed response of the synchronous firing of the nerve fibers in response to the acoustic stimuli, and it appears as an alternating current voltage. The auditory nerve Action Potential is characterized by a series of brief, predominantly negative peaks, including a first negative peak (N1) and second negative peak (N2). The auditory nerve Action Potential also includes a magnitude and a latency. The magnitude of the auditory nerve Action Potential reflects the number of fibers that are firing, while the latency of the auditory nerve Action Potential is measured as the time between the onset and the first negative peak (N1).

FIG. 2 is a flowchart illustrating operations performed by the ECoG-based programming module 118 during use of one or more of the above components of a measured ECoG response to in-situ program (i.e., determine and set) comfort levels for the recipient at the stimulating contacts 138 in accordance with embodiments presented herein.

The method 150 of FIG. 2 begins at 152 where the ECoG-based programming module 118 determines a reference ECoG response (i.e., a reference set of acoustically-induced electrical potentials) for a recipient's cochlea. In particular, at 152, the ECoG-based programming module 118 instructs the sound processor 112 to deliver only acoustic stimulation (i.e., no electrical stimulation) to the recipient via the receiver 142. The acoustic stimulation, which is referred to herein as "acoustic test stimulation," is generally a pure tone pulsed signal (i.e., delivered at a set frequency) that has a substantially fixed (constant) intensity (acoustic amplitude). As described further below, the intensity and frequency of the acoustic test stimulation may vary depending on a variety of factors, such as recipient-specific characteristics (e.g., age, type or degree of hearing loss, etc.), stimulating contact position, etc.

In response to delivery of the acoustic test stimulation, the ECoG-based programming module 118 performs an ECoG measurement using one or more of the intra-cochlear stimulating contacts 138. That is, an initial ECoG measurement is performed in the presence of acoustic stimulation only (no electrical stimulation). The result of this initial ECoG measurement is the above-mentioned reference ECoG response that represents the baseline ECoG response of the recipient's cochlea (i.e., the baseline response of the cochlea to the acoustic test stimulation). This baseline response may characterize the morphology, magnitude, frequency composition and phase of the acoustically-induced cochlear potentials in an effort to capture all aspects of the recorded response when the stapedius is not in activation. The cochlear potentials forming the reference ECoG response are obtained by one or more amplifiers 143 (FIG. 1B) located in the implantable component 104 and then are transmitted back to the external component 102 for storage and subsequent use (i.e., integrated amplifier of the cochlear implant captures one or more recording windows of the evoked activity and sends this via telemetry (wirelessly) back to the sound processing unit 110).

After the reference ECoG response is obtained, at 154 the electro-acoustic hearing prosthesis 100 continues or restarts delivery of the acoustic test stimulation to the recipient. At this point, and until method 150 is terminated at 170, the acoustic test stimulation is delivered to the recipient continuously. That is, the operations of 154-168 are generally performed while the acoustic test stimulation is delivered to the recipient.

At 156, the ECoG-based programming module 118 instructs the stimulator unit 132 to deliver electrical stimulation (current pulses) to the recipient at (via) a selected intra-cochlear stimulating contact 138. The electrical stimulation, which is referred to herein as electrical test stimulation, is first delivered at an initial level (current level). In response to delivery of the electrical test stimulation, the ECoG-based programming module 118 performs an ECoG measurement to obtain a measured ECoG response. This measured ECoG response represents the cochlea potentials evoked in the cochlea by the acoustic test signal in the presence of the electrical test stimulation at the initial current level. The measured ECoG response is obtained by one or amplifiers 143 (FIG. 1B) located in the implantable component 104 and then are transmitted back to the external component 102 for storage and subsequent use.

At 160, the ECoG-based programming module 118 compares the measured ECoG response to the reference ECoG response (e.g., determines whether the measured ECoG response is has altered significantly from the reference ECoG response). More specifically, in the embodiment of FIG. 2, the ECoG-based programming module 118 compares one or more of the morphology, magnitude, frequency aspects, phase, temporal aspects, etc. of the measured ECoG response and the reference ECoG response.

In accordance with embodiments presented herein, a difference between the measured ECoG response and the reference ECoG response indicates that the acoustic impedance of the tympanic membrane (or eardrum) has changed due to activation of the stapedius reflex. More specifically, the stapedius reflex is an involuntary muscle contraction of the stapedius muscle that, in accordance with embodiments presented herein, is triggered by the delivery of electrical stimulation that evokes an auditory percept of sufficient loudness. In other words, when the electrical test stimulation is of sufficient magnitude, the stapedius reflex is activated. Activation of the stapedius reflex decreases the compliance of the ossicular chain and the tympanic membrane (i.e., increases acoustic impedance). This compliance change, in turn, reduces the intensity of the acoustic signal delivered to the inner ear via the ossicular chain, thereby altering the e measured ECoG response relative to the reference ECoG response without delivery of electrical stimulation.

The activation of the stapedius reflex is also correlated to the upper bounds of the recipient's comfort level. That is, when delivering electrical stimulation to evoke a hearing percept, the stimulation should generally be delivered at amplitudes that do not evoke the stapedius reflex. Therefore, in the example of FIG. 2, if it is determined at 160 that the measured ECoG response is different from the reference ECoG response, then at 162 the ECoG-based programming module 118 stores the level of the delivered electrical test stimulation as the comfort level for the recipient at the associated stimulating contact (i.e., the stimulating contact used to deliver the electrical test stimulation). Stated differently, since delivery of the electrical test stimulation evoked the stapedius reflex (as indicated by the change in the ECoG response), the level of the electrical test stimulation indicates the maximum current level that should be used for hearing rehabilitation as higher current levels will activate the stapedius reflex.

If it is determined at 160 that the measured ECoG response is substantially the same as the reference ECoG response, then method 150 proceeds to 164 where the current level of the electrical test stimulation is incremented (increased). The method returns to 156 where the electrical test stimulation is redelivered at the increased level. The operations of 158, 160, 164, and 156 are repeated until it is determined at 160 that one or more of the morphology, magnitude, frequency composition, phase, etc. of the measured ECoG response is different from that of the reference ECoG response.

In other words, the iterative operations of 156, 158, 160, and 164 illustrate that sets or groups of electrical stimulation are sequentially delivered to the recipient via a selected intra-cochlear stimulating contact at incrementally increasing current levels (i.e., each group of electrical test stimulation has an increased current level relative to the prior group of electrical test stimulation). ECoG measurements are made in response to the delivery of each group of electrical test stimulation and analyzed for determination of whether there has been a change in the acoustic impedance due to activation of the stapedius reflex. It is to be appreciated that the electrical stimulation delivered in accordance with embodiments presented herein may take a number of different forms, such as groups of one or more pulses, modulated pulse trains, multiple contact stimulation, such as phased array, tripolar, etc.

The current level of the electrical test stimulation is likely to be initially set at a relatively low current level so that the recipient's stapedius reflex is not evoked at the first ECoG measurement. Therefore, in practice, the method 150 would complete several iterations of 156, 158, 160, and 164 before it is determined that the measured ECoG response is different from the reference ECoG response. Starting with a low initial current level for the electrical test stimulation ensures that the comfort level is not accidentally set at too high of a level. In certain embodiments, a determination at 160 that the measured ECoG response is different from the reference ECoG response during a first comparison may trigger an error condition that causes the method to be re-started at a lower initial current level for the electrical test stimulation.

As noted elsewhere herein, comfort levels vary across a recipient's stimulating contacts and there is a need to set comfort levels for each of the intra-cochlear stimulating contacts 138. Therefore, returning to 162, once the current level is set for the initially chosen stimulating contact, the method 150 proceeds to 168 where a determination is made whether comfort levels have been programmed for a selected number of the stimulating contacts. If so, the method 150 ends at 170.

However, if it is determined at 168 that comfort levels have not been programmed for the selected number of the stimulating contacts, then the method 150 proceeds to 166 where another stimulating contact is chosen for testing. The operations of 156, 158, 160, 164, and, ultimately 162 are then repeated for this newly chosen stimulating contact until the comfort level for the newly chosen stimulating contact is programmed. This iterative process is re-triggered at 168 until comfort levels have been determined for the selected number of contacts where, thereafter, the method 150 ends at 170. Upon reaching 170, the acoustic test stimulation is terminated.

It is to be appreciated that comfort levels do not necessarily need to be programmed as described above with reference to FIG. 2, for all stimulating contacts implanted in a recipient. Instead, the comfort levels for only subset of implanted stimulating contacts may be programmed as described above with reference to FIG. 2 and the subset of comfort levels may then be used to extrapolate or otherwise estimate the comfort levels of the remaining stimulating contacts. That is, one or more of the comfort levels may be programmed through an estimation process that makes use of comfort levels that are measured as described above.

In summary of FIG. 2, an acoustic signal is delivered to the recipient and a baseline/reference in-situ measurement of the ECoG response is acquired. The acoustic signal is maintained at a fixed intensity, and electrical stimulation is delivered on a given stimulating contact and increased in current level (CL) steps. At each current level step, the evoked ECoG response is measured. The one or more of aforementioned characteristics of the measured ECoG response are compared against the characteristics of the reference ECoG response and, if there is a significant change, the current of the electrical stimulus for the given stimulating contact is stored at the comfort level for that stimulating contact. The process is then repeated for a number of remaining contacts and an electrical comfort level or 'upper-limit' profile (i.e., comfort levels for all of the stimulating contacts) for the recipient is derived.

In accordance with embodiments presented herein, a selected stimulating contact 138 is used to deliver the electrical test stimulation, while one or more other (different) stimulating contacts 138 are used to perform the ECoG measurements. The one or more stimulating contacts 138 selected for performance of the ECoG measurements may vary in different embodiments based on, for example, relative position or proximity to the contact delivering the electrical test stimulation, recipient characteristics, etc. In one embodiment, the most apical stimulating contact may be used to perform substantially all of the ECoG measurements.

In other embodiments, the stimulating contacts are evaluated and the one determined to provide the largest ECoG response is selected for use in the ECoG measurements. More specifically, ECoG-based programming module 118 may be configured to automatically select a stimulating contact for ECoG measurements and to automatically select the appropriate frequency of acoustic test stimulation for use in determining the comfort level for the stimulating contact. In one illustrative such arrangement, the electro-acoustic hearing prosthesis 100 is configured to deliver a 250 Hz tone and then perform ECoG measurements at one or more of the stimulating contacts 138. The electro-acoustic hearing prosthesis 100 may then deliver a 500 Hz tone and repeat the ECoG measurements at the one or more stimulating contacts. This process may be repeated at other tones (e.g., repeat for 750 Hz and so on). The electro-acoustic hearing prosthesis 100 could then compare the amplitudes of the measured ECoG responses across the one or more stimulating contacts and frequency sets to select the contact/frequency combination yielding the maximum cochlear microphonic.

In one specific technique in accordance with embodiments presented herein, a recipient is implanted with a stimulating assembly that includes twenty-two (22) spaced stimulating contacts, referred to as stimulating contacts 1 to 22. A pulsed acoustic pure tone signal (acoustic test stimulation) is delivered to the recipient with an intensity of approximately 70 dBSPL at 250 Hz, which is an acoustic input level that is known to not activate the stapedius reflex for the recipient. In response, an ECoG measurement is performed at the most distal (apical) stimulating contact (i.e., stimulating contact 22) to determine a reference ECoG response for the recipient. Subsequently, while the acoustic pure tone signal is delivered to the recipient, an electrical stimulus (electrical test stimulation) is delivered, for example, at a stimulating contact 17. An ECoG measurement is then performed at stimulating contact 22 to obtain a measured ECoG response. In this example, stimulating contact 17 is sufficiently spaced from electrode 22 so that the stimulation artefacts from the electrical stimulus do not corrupt the ECoG recording. In certain embodiments, the electrical stimulation can be delivered prior to the ECoG response recording (e.g., 0.5 ms before the recording) because the stapedius reflex will remain after the electrical stimulus as there is a latency of approximately 20-30 ms post stimulus to account for the transconduction of the signal up the auditory pathway to the mid-brain and back to the stapedius muscle.

As noted above, the electrical stimulation that is delivered to a recipient may have any of a number of different forms. In one specific example, the electrical stimulation may be a pulse train of 0.5 ms length pulses with a rate reflective of the clinical map. In certain examples, the ECoG response is measured several times in response to the same electrical stimulus (e.g., 5 times) to enable generation of an averaged measured ECoG response. The averaged measured ECoG response could then be compared to the reference ECoG response for evaluation of whether the level of the electrical response is at the comfort level. An average could also be determined in a similar manner for the reference ECoG response.

As noted, if there is substantially no difference between the measured ECoG response (e.g., an averaged ECoG response) and a reference ECoG response, then the current level of the electrical stimulus is incremented. After each current level increment, a comparison of a newly measured ECoG response to the reference ECoG response is performed until a difference there between is identified. In one example, if a change of greater than a selected threshold, e.g. 3 dB, is observed, then the measurement is repeated at the same current level. If a second positive result occurs (i.e., the difference again exceeds the threshold), then a flag is set for the stimulating contact and the current level. The process may then be repeated for other stimulating contacts, as described above.

In recipients with residual hearing, there is often a region of the cochlea, sometimes referred to herein as the cut-off region, in which acoustic stimulation overlaps with electrical stimulation. That is, in this cut-off region, both acoustic and electrical stimulation are perceived by the recipient and, as a result, it is possible that sounds may be perceived as relatively "louder" within this region.

Certain embodiments presented herein are directed to setting comfort levels for stimulating contacts within the cut-off region to account for the presence of the acoustic stimulation. More specifically, for stimulating contacts estimated to reside in the recipient's cut-off region, a complex tone (e.g., a two frequency tone at 250 Hz and 750 Hz) acoustic signal is delivered to the recipient. One tonal component of the complex tone (e.g., the 250 Hz component) is used to track the stapedius reflex activity, while the second tonal component (e.g., the 750 Hz component) is combined with the electrical stimulation on a stimulating contact mapped to this frequency for the recipient. As a result, subsequent ECoG measurements represent the response of the recipient's cochlea to both the electrical stimulation and the second tonal component of the complex tone. This allows the system to assess the affects of the overlap of the acoustic stimulation with electrical stimulation. In other words, these techniques allow for the determination of refined comfort levels that account for the affects of electro-acoustic stimulation (i.e., electrical stimulation in combination with acoustic stimulation), rather than only the affects of electrical stimulation.

FIGS. 1A, 1B, and FIG. 2 illustrate an embodiment in which acoustic test stimulation is delivered via a receiver 142 forming part of the electro-acoustic hearing prosthesis 100. However, as noted above, embodiments of the present invention may be implemented in other types of hearings prosthesis and hearing prosthesis systems (e.g., arrangements in which a hearing prosthesis operates with an external device that is separate from the hearing prosthesis), including arrangements in which the hearing prosthesis does not include a built-in receiver to deliver acoustic stimulation. In such embodiments, the acoustic test stimulation may be delivered by a receiver that is part of the external device that is separate from the hearing prosthesis, such as a receiver forming part of a computer or mobile device (e.g., mobile phone, tablet computer, etc.). In certain such embodiments, the external device communicates with the hearing prosthesis to initiate, modify, terminate, etc. the delivered acoustic test stimulation.

FIGS. 1A, 1B, and FIG. 2 have also been described with reference to use of electrical stimulation to trigger the recipient's stapedius reflex. However, it is to be appreciated that in alternative embodiments presented herein the stapedius reflex can be evoked through the delivery of acoustic stimulation. For example, in one illustrative example, an acoustic stimulation (e.g., a pure tone at 70 dBSPL) is first delivered to the recipient and an ECoG response is measured to create a reference ECoG response. The level of the acoustic stimulation is then gradually and incrementally increased and an ECoG response is measured at each step increase. The measured ECoG responses are compared to the reference ECoG response to identify, for example, changes in the waveshape, etc. that would not be expected during an increase in the delivered acoustic level, thereby indicating the triggering of the recipient's stapedius reflex. Once the stapedius reflex is detected, a new frequency would then be chosen and the process repeated so as to create a comfort level profile. In other words, in these embodiments, acoustic stimulation is used to both trigger the recipient's stapedius reflex as well as to detect the resulting change in acoustic impedance via changes in the ECoG response.

As described above, the embodiments presented herein rely upon an indirect relationship between ECoG responses and the stapedius reflex (i.e., changes in the ECoG response due to the delivery of stimulation is linked to the stapedius reflex as the delivered stimulation changes the compliance of the round window and changes the sensitivity of the hair cells to acoustic stimulation). This indirect relationship is schematically shown in FIGS. 3A and 3B. More specifically, FIGS. 3A and 3B are schematic diagrams that each includes four (4) sections 174, 176, 178, and 180. The section 174 schematically illustrates the electrical test stimulation that may be delivered to a recipient in accordance with embodiments presented herein. In FIG. 3A, the electrical stimulation is delivered at a current level that is relatively low compared to the electrical stimulation delivered in FIG. 3B.

Section 176 describes the ear drum compliance observed in response to the electrical stimulation of section 174. As shown, the ear drum compliance is "neutral" in FIG. 3A, but is "decreased" in FIG. 3B. In other words, in FIG. 3A, the compliance of the ear drum is not affected by the electrical test stimulation, while in FIG. 3B the delivered electrical test stimulation has altered (decreased) the ear drum compliance. That is, the stapedius reflex has been activated (evoked).

Section 178 illustrates that the ECoG responses, namely the cochlear microphonics, measured in response to the electrical test stimulation of section 174, in the presence of acoustic stimulation (not shown in FIGS. 3A and 3B). As shown, the measured cochlear microphonic of FIG. 3A has a larger amplitude than the amplitude of the measured cochlear microphonic of FIG. 3B. Finally, section 180 illustrates a status or state of the stapedius reflex in response to the electrical test stimulation. In FIG. 3A, the stapedius reflex is inactive, while in FIG. 3B the stapedius reflex is activate. In other words, FIGS. 3A and 3B illustrate that when the electrical test stimulation is of sufficient magnitude, the stapedius reflex is activated. Activation will decrease the compliance of the ossicular chain (increase acoustic impedance). The compliance change will, in turn, reduce the intensity of the acoustic signal delivered to the inner ear, thereby reducing the ECoG amplitude.

As noted above, in accordance with embodiments presented herein, a constant (known) acoustic test stimulation is applied to a recipient at a fixed intensity/amplitude. In general, the acoustic test stimulation has an amplitude that is sufficient to evoke a measurable ECoG response (e.g., measurable cochlear microphonic), but that does not activate the stapedius reflex. In individuals with normal (non-impaired) hearing, the stapedius reflex is triggered for sounds in the range of 75-90 dBSPL. For the hearing impaired with losses in the low frequencies, the stapedius reflex threshold will be elevated according the level of the loss. As some recipients have near to normal hearing in the low frequencies, the initial acoustic test stimulation may be kept, for example, at a constant 70 dBSPL at the frequency of delivery. This would also ensure comfort for the recipient undergoing the programming.

Figure 4:
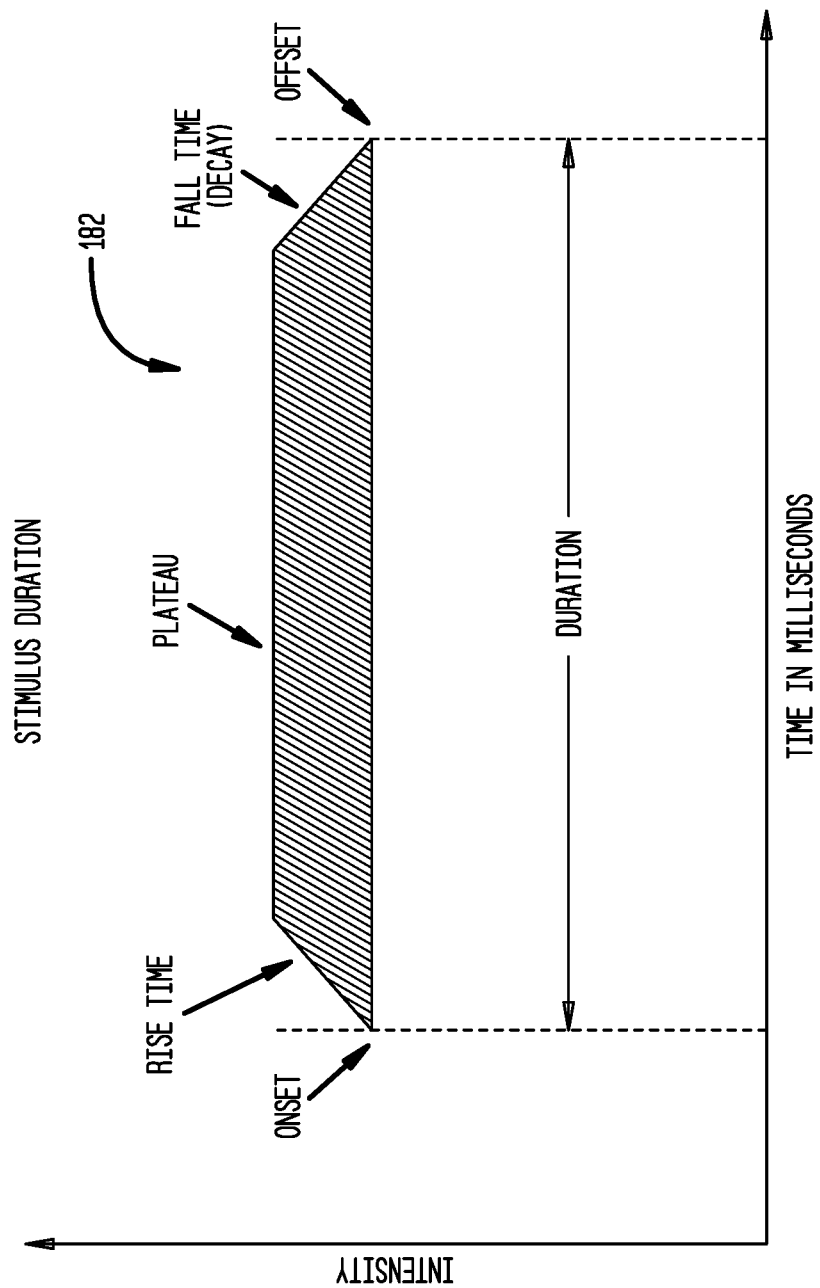
FIG. 4 is a schematic diagram illustrating an acoustic stimulation pulse in accordance with embodiments presented herein.

The acoustic test stimulation, although delivered at affixed amplitude, is a pulsed signal. FIG. 4 is a diagram illustrating an example pure tone acoustic test stimulation pulse 182 that may be employed in accordance with embodiments presented herein. In the example of FIG. 4, the input frequency is a default 500 Hz. However, as described further below, the frequency may be customized based on, for example, the insertion depth of a stimulating contact and/or other parameters.

In the example of FIG. 4, the rise and fall times of the acoustic test stimulation pulse 182 are each approximately 35 milliseconds (ms) respectively. The acoustic test stimulation pulse 182 has a plateau of approximately 20-40 ms (i.e., sufficient to capture the input frequency). As such, the net duration of the acoustic test stimulation pulse 182 (i.e., the rise+plateau+fall times) is approximately 90-110 ms.

As noted, different parameters may affect the parameters of an acoustic test stimulation that is delivered to a recipient in accordance with embodiments presented herein. In one example, the insertion depth of the stimulating contact (electrode) that is under test may influence, for example, the acoustic frequency of the acoustic test stimulation. For example, a relative position of the most apical stimulating contact e to the site of excitation of the outer hair cells in the cochlea (responding to the acoustic input) is likely to dictate the measured cochlear microphonic amplitude. Therefore, for deeper insertions in the cochlea (e.g., greater than 360 degrees), a lower frequency may be used, while a higher frequency may be used for shallower insertions. Therefore, in accordance with certain embodiments presented herein, an ECoG-based programming module may vary or change the acoustic test stimulation used for different stimulating contacts.

Figure 5:
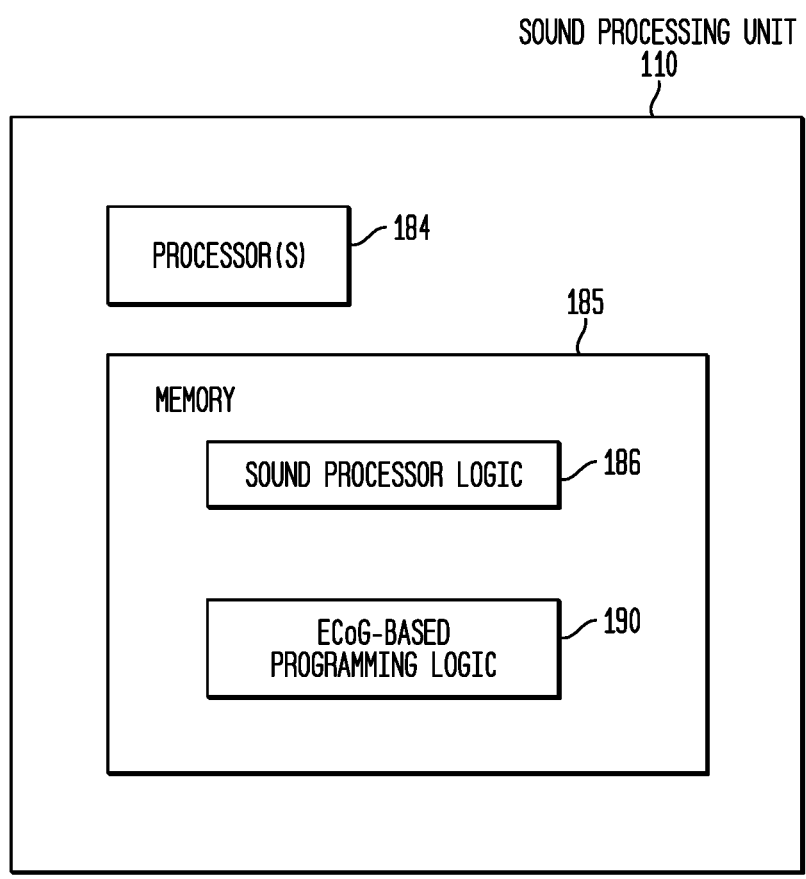
FIG. 5 is a block diagram of a sound processing unit in accordance with embodiments presented herein.

FIG. 5 is a schematic block diagram illustrating an arrangement for a sound processing unit, such as sound processing unit 110, in accordance with an embodiment of the present invention. As shown, the sound processing unit 110 includes one or more processors 184 and a memory 185. The memory 185 includes sound processor logic 186 and ECoG-based programming logic 190.

The memory 185 may be read only memory (ROM), random access memory (RAM), or another type of physical/tangible memory storage device. Thus, in general, the memory 185 may comprise one or more tangible (non-transitory) computer readable storage media (e.g., a memory device) encoded with software comprising computer executable instructions and when the software is executed (by the one or more processors 184) it is operable to perform the operations described herein with reference to sound processor 112 and ECoG-based programming module 118.

FIG. 5 illustrates software implementations for the sound processor 112 and the sound ECoG-based programming module 118 that makes use of onboard digital signal processors (DSPs) or microprocessors. However, it is to be appreciated that one or more operations associated with the sound processor 112 and/or the ECoG-based programming module 118 may be partially or fully implemented with digital logic gates in one or more application-specific integrated circuits (ASICs).

Merely for ease of illustration, the ECoG-based programming module 118 has been shown and described as elements that are separate from the sound processor 112. It is to be appreciated that the functionality of the ECoG-based programming module 118 may be incorporated into the sound processor 112.

In addition, FIG. 5 illustrates an arrangement in which the ECoG-based programming module 118 is fully integrated in a hearing prosthesis (i.e., a fully integrated in-situ stapedius reflex measurement). However, as noted elsewhere herein, the techniques presented herein may be implemented in hearing prosthesis systems where some of the operations described above (e.g., the operations of the ECoG-based programming module 118) are performed by an external device operating with the hearing prosthesis. For example, the acoustic test stimulation may be delivered by a receiver that is part of the external device that is separate from the hearing prosthesis, such as a receiver forming part of a computer or mobile device (e.g., mobile phone, tablet computer, etc.). In certain embodiments, the analysis of ECoG responses (e.g., comparisons of measured ECoG responses to a reference ECoG response) may be formed by the external device and/or the external device.

Figure 6:
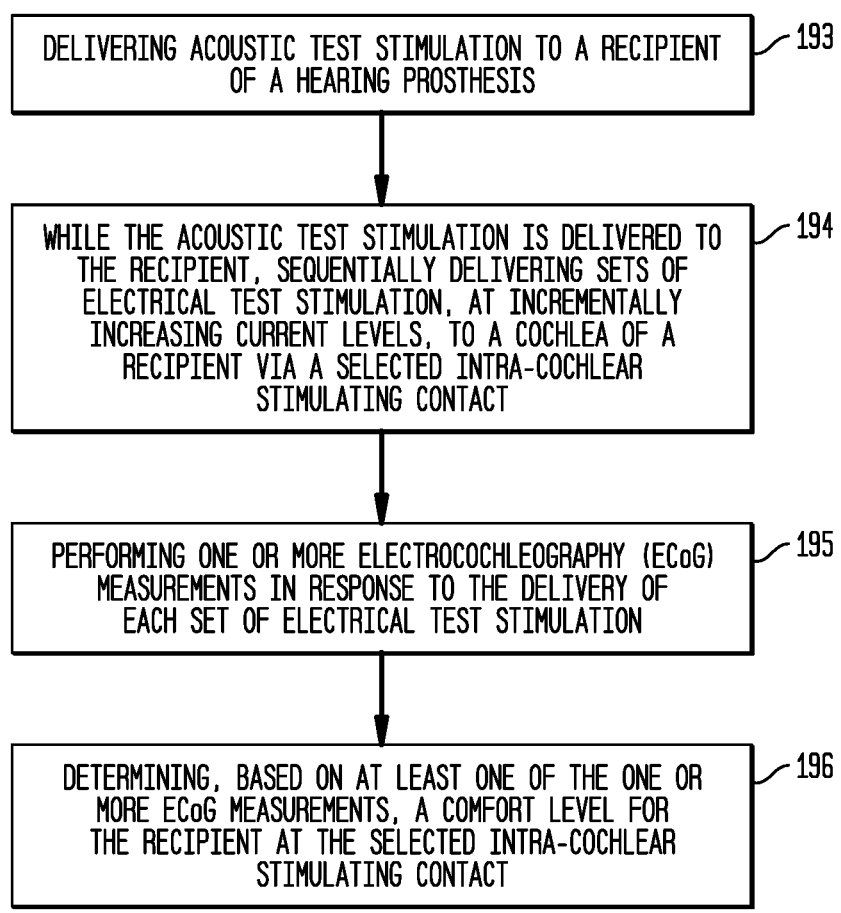
FIG. 6 is a high-level flowchart of a method in accordance with embodiments presented herein.

FIG. 6 is a flowchart of a method 192 in accordance with embodiments presented herein. Method 192 begins at 193 where acoustic test stimulation is delivered to a recipient of a hearing prosthesis. At 194, while the acoustic test stimulation is delivered to the recipient, sets of electrical test stimulation are sequentially delivered, at incrementally increasing current levels, to a cochlea of a recipient via a selected intra-cochlear stimulating contact. At 195, one or more ECoG measurements are performed in response to the delivery of each set of electrical test stimulation. At 196, based on at least one of the one or more ECoG measurements, a comfort level for the selected intra-cochlear stimulating contact is determined.

Figure 7:
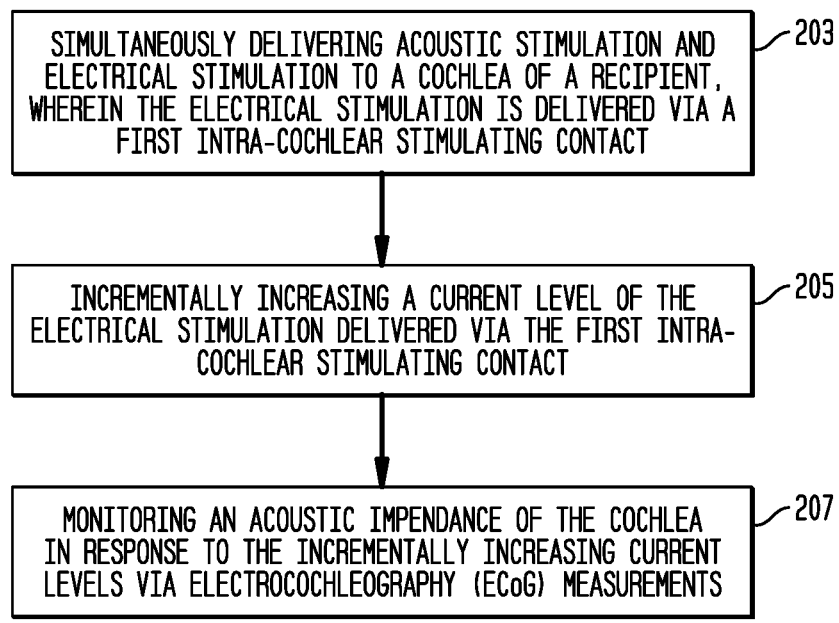
FIG. 7 is a high-level flowchart of another method in accordance with embodiments presented herein.

FIG. 7 is a flowchart of another method 201 in accordance with embodiments presented herein. Method 201 begins at 203 where acoustic stimulation and electrical stimulation are simultaneously delivered to a cochlea of a recipient. The electrical stimulation is delivered via a first intra-cochlear stimulating contact. At 205, a current level of the electrical stimulation delivered via the first intra-cochlear stimulating contact is incrementally increased. At 207, an acoustic impedance of the cochlea in response to the incrementally increasing current levels is monitored via electrocochleography (ECoG) measurements. A comfort level for the first intra-cochlear stimulating contact may then be determined based on the ECoG measurements.

As detailed above, the techniques presented herein use acoustically evoked electrocochleography (ECoG) to indirectly monitor the activity of the stapedius muscle contraction, and hence the onset of the stapedius reflex, so as to enable determination of a comfort level profile for a recipient. When executed at a hearing prosthesis, the techniques presented herein provide a fully-integrated indirect measure of the stapedius reflex that can be performed using either ear of the individual. These techniques allow the recipient to move during the programming process and are substantially automated so that the programming can be performed remotely and without the need for specialized skills (i.e., direct involvement by an audiologist).

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
   delivering acoustic test stimulation to a recipient of a hearing prosthesis;
   while the acoustic test stimulation is delivered to the recipient, sequentially delivering sets of electrical test stimulation, at incrementally increasing current levels, to a cochlea of a recipient via a selected intra-cochlear stimulating contact;
   performing one or more electrocochleography (ECoG) measurements in response to the delivery of each set of electrical test stimulation; and
   determining, based on at least one of the one or more ECoG measurements, a comfort level for the recipient at the selected intra-cochlear stimulating contact.

2. The method of claim 1, wherein determining a comfort level for the recipient at the selected intra-cochlear stimulating contact comprises:
   determining, based on at least one of the one or more ECoG measurements, a current level of electrical test stimulation that activates a stapedius reflex in the recipient.

3. The method of claim 1, wherein delivering acoustic test stimulation comprises:
   delivering a complex tone comprising at least one tonal component configured to combine with the electrical test stimulation,
   wherein the one or more electrocochleography measurements represent a response of the recipient's cochlea to both the electrical test stimulation and the least one tonal component of the complex tone.

4. The method of claim 3, further comprising determining a reference ECoG measurement, wherein the reference ECoG measurement is a measurement of electrical potentials induced in the cochlea of the recipient in response to delivery of only the acoustic test stimulation to the recipient.

5. The method of claim 1, wherein determining a comfort level for the recipient at the selected intra-cochlear stimulating contact comprises:
   detecting, based on the ECoG measurements, an acoustic impedance change of the cochlea of the recipient.

6. The method of claim 1, wherein the hearing prosthesis is an electro-acoustic hearing prosthesis, and wherein the acoustic test stimulation is delivered by the electro-acoustic hearing prosthesis.

7. The method of claim 1, wherein delivering the acoustic test stimulation to the recipient comprises:
   delivering a pure tone pulsed acoustic signal with a substantially fixed intensity.

8. A method, comprising:
   simultaneously delivering acoustic stimulation and electrical stimulation to a cochlea of a recipient, wherein the electrical stimulation is delivered via a first intra-cochlear stimulating contact;
   incrementally increasing a current level of the electrical stimulation delivered via the first intra-cochlear stimulating contact; and
   monitoring an acoustic impedance of the cochlea in response to the incrementally increasing current levels via electrocochleography (ECoG) measurements.

9. The method of claim 8, further comprising:
   determining a comfort level for the recipient at the first intra-cochlear stimulating contact based on the ECoG measurements.

10. The method of claim 9, further comprising:
    delivering the electrical stimulation via a second intra-cochlear stimulating contact that is different from the first intra-cochlear stimulating contact,
    incrementally increasing the current level of the electrical stimulation delivered via the second intra-cochlear stimulating contact; and
    monitoring, based on one or more additional ECoG measurements, the acoustic impedance of the cochlea in response to the incrementally increasing current levels of the electrical stimulation delivered via the second intra-cochlear stimulating contact to determine a comfort level for the recipient at the second intra-cochlear stimulating contact.

11. The method of claim 10, further comprising:
generating a comfort level profile for the recipient based at least on the comfort level for the recipient at the first intra-cochlear stimulating contact and the comfort level for the recipient at the second intra-cochlear stimulating contact.

12. The method of claim 8, further comprising:
prior to simultaneously delivering acoustic stimulation and electrical stimulation to the cochlea of a recipient, determining a reference ECoG measurement, wherein the reference ECoG measurement is a measurement of electrical potentials induced in the cochlea of the recipient in response to delivery of only the acoustic stimulation to the recipient.

13. The method of claim 8, wherein the acoustic stimulation and the electrical stimulation are each delivered by an electro-acoustic hearing prosthesis.

14. A hearing prosthesis system, comprising:
a receiver configured to deliver an acoustic signal to a cochlea of a recipient;
a plurality of stimulating contacts configured to be positioned in the cochlea of the recipient, wherein a first one of the plurality of stimulating contacts is configured to sequentially deliver groups of current pulses to the cochlea at incrementally increasing current levels;
one or more amplifiers configured to obtain, via at least a second one of the plurality of stimulating contacts, acoustically-evoked cochlear potentials from the cochlea following delivery of each group of current pulses; and
one or more processors configured to determine, based on the acoustically-evoked cochlear potentials, an upper limit of a dynamic range associated with the first stimulating contact.

15. The hearing prosthesis system of claim 14, wherein to determine the upper limit of the dynamic range associated with the first stimulating contact, the one or more processors are configured to:
determine, based on the acoustically-evoked cochlear potentials, a current level of the current pulses that activates a stapedius reflex in the recipient.

16. The hearing prosthesis system of claim 15, wherein the acoustically-evoked cochlear potentials include measured cochlear microphonics, and wherein to determine a current level of the current pulses that activates a stapedius reflex in the recipient, the one or more processors are configured to:
compare a magnitude of a measured cochlear microphonic to a magnitude of a reference cochlear microphonic.

17. The hearing prosthesis system of claim 16, wherein the reference cochlear microphonic is determined based on delivery of only the acoustic signals to the recipient.

18. The hearing prosthesis system of claim 14, wherein to determine the upper limit of the dynamic range associated with the first stimulating contact, the one or more processors are configured to:
detect, based on the acoustically-evoked cochlear potentials, an acoustic impedance change of the cochlea of the recipient.

19. The hearing prosthesis system of claim 14, wherein the hearing prosthesis is an electro-acoustic hearing prosthesis, and wherein the acoustic test stimulation is delivered by the electro-acoustic hearing prosthesis.

20. The hearing prosthesis system of claim 14, wherein the acoustic signal comprises a pure tone pulsed acoustic signal with a substantially fixed intensity.

* * * * *